United States Patent [19]
Lynch et al.

[11] Patent Number: 5,998,152
[45] Date of Patent: Dec. 7, 1999

[54] HIGH-THROUGHPUT SCREENING ASSAYS FOR MODULATORS OF NUCLEIC ACID TOPOISOMERASES

[75] Inventors: Anthony Simon Lynch, Pacifica; Binoj Joseph Matthew, Daly City, both of Calif.

[73] Assignee: Tularik Inc., South San Francisco, Calif.

[21] Appl. No.: 09/037,154

[22] Filed: Mar. 9, 1998

[51] Int. Cl.$^6$ .............................. G01N 33/53; C12N 9/90
[52] U.S. Cl. ............................................. 435/7.1; 435/233
[58] Field of Search ...................................... 435/7.1, 233

[56] References Cited

U.S. PATENT DOCUMENTS 5,645,994   7/1997   Huang ........................................ 435/6

OTHER PUBLICATIONS

Muller et al., Nucleic Acids Res., 17 (22), "A Rapid and Quantitative Microtieter Assay for Eukaryotic Topoisomerase II", p. 9499, 1989.
Shin et al., Teratog Carcinog Mutagen, 10(1), "Rapid Evaluation of Topoisomerase Inhibitors Caffeine Inhibition of Topoisomerases in–vivo", pp. 41–52, 1990.
Andrea et al., Mol Pharmacol, 40(4), "Fluorometric Assays for DNA Topoisomerases and Topoisomerase–targeted Drugs Quantitation of Catalytic Activity and DNA Cleavage", pp. 495–501, 1991.
Miyahara et al., Food Factors Cancer Prev., [Int. Conf.] , Meeting Date 1995, "Some Phytochemicals and Related Compounds in Vegetables as Potent Inhibitors of Human DNA Topoisomerase II", pp. 182–187. Editor(s): Ohigashi, Hajime. Publisher: Springer, 1997.
Sittampalam et al., Current Opinion in Chemical Biology, vol. 1, No. 3, "High–throughput Screening: Advances in Assay Technologies", pp. 384–391, Oct. 1997.
Silverman et al., Current Opinion in Chemical Biology, vol. 2, No. 3, "New Assay Technologies for High–throughput Screening", pp. 397–403, Jun. 1998.
Barrett et al., Analytical Biochemistry (1993) 214: 313–317.
Barrett et al., Antimicrobial Agents and Chemotherapy (Jan. 1990) 34(1): 1–7.
Condemmie et al., Nucleic Acids Res. (1990) 18: 7389–7397.
Drlica et al., Microbiol. Mol. Biol. Rev. (1997) 61: 377–392.
Elsea et al., Am. J. Med. Genet. (1998) 75: 104–108.
Fisher et al., Proc. Natl. Acad. Sci. U.S.A. (1981) 78: 4165.
Franco et al., J. Mol. Biol. (1988) 201: 229–233.
Froelich–Ammon et al., J. Biol. Chem. (1995) 270: 21429–21432.
Hanai et al., Proc. Nat. Acad. Sci. (1996) 93: 3653–3657.
Jenkins et al., Nucleic Acids Res. (1992) 20: 5587–5592.
Kato et al., Cell (1990) 63: 393–404; erratum Cell (1991) 65: 1289.
Kirkegaard et al., Cell (1981) 23: 721.
Kowalski, Analytical Biochemistry (1980) 107: 311–313.
Lerner et al., Journal of Biomolecular Screening (1996) 1(3): 135–143.
Lerner et al., Analytical Biochemistry (1996) 240: 185–196.
Lockshon et al., J. Mol. Biol. (1985) 181: 63.

(List continued on next page.)

Primary Examiner—Jon P. Weber
Attorney, Agent, or Firm—Townsend and Townsend and Crew LLP

[57] ABSTRACT

This invention provides novel assays for topoisomerase activity and for identifying topoisomerase inhibitors. The assays include both solid-phase and liquid-phase methods that are amenable to high throughput screening methods. The assays of the invention are readily adaptable to numerous types of topoisomerase, and are capable of identifying novel classes of topoisomerase activity modulators.

16 Claims, 7 Drawing Sheets

OTHER PUBLICATIONS

Maxwell, *Mol. Microbiol.* (1993) 9: 681–686.

Miller et al., *Cell* (1990) 62: 127–133.

Morrison et al., *Proc. Natl. Acad. Sci. U.S.A.* (1981) 78: 1416–1420.

O'Connor et al., *J. Mol. Biol.* (1985) 181: 545.

Pato et al., *Proc. Natl. Acad. Sci. U.S.A.* (1990) 87: 8716–8720.

Anderson, et al., "Studies of the topoisomerase II–mediated cleavage and religation reactions by use of a suicidal double–stranded DNA substrate" *J. Biol. Chem.* 266(14):9203–9210 (1991).

Burgin et al. "A novel suicide substrate for DNA topoisomerases and site–specific recombinases" *Nucleic Acids Res.* 23 (15):2973–1979 (1995).

Jensen, et al. "Purification and characterization of human topoisomerase I mutants" *Eur. J. Biochem.* 236(2):389–394 (1996).

Kjeldsen et al. "Camptothecin inhibits both the cleavage and religation reactions of eukaryotic DNA topoisomerase I." *J. Mol. Biol.* 228(4):1025–1030 (1992).

Pargellis, et al. "Suicide recombination substrates yield covalent lambda integrase–DNA complexes and lead to identification of the active site tyrosine" *J. Biol. Chem.* 263(16):7678–85 (1988).

Pourquier, et al. "Effects of uracil incorporation, DNA mismatches, and abasic sites on cleavage and religation activities of mammalian topoiisomerase I." *J. Biol. Chem.* 272(12):7792–7796 (1997).

Pourguier, et al. "Trapping of mammaliam topoisomerase I and recombinations induced by damaged DNA containing nicks or gaps" *J. Biol. Chem.* 272(42):26441–26447 (1997).

Stewart, et al. "Reconstitution of human topoisomerase I by fragment complementation" *J. Mol. Biol.* 269(3):355–372 (1997).

Svejstrup, et al. "New technique for uncoupling the cleavage and religation of eukaryotic topoisomerase I." *J. Mol. Biol.* 222(3):669–78 (1991).

Tirumalai, et al. "The catalytic domain of lambda site–specific recombinase" *Proc. Nat'l. Acad. Sci. USA* 94(12):6104–6109 (1997).

Pommier et al., *Biochemistry* (1985) 24(23): 6410–6416.

Reece et al., *Crit. Rev. Biochem. Mol. Biol.* (1991) 26: 335–375.

Roca et al., *Proc. Natl. Acad. Sci. U.S.A.* (1994) 91: 1781–1785.

Sørensen et al., *J. Mol. Biol.* (1992) 228: 778–786.

Tsai–Pflugfelder et al., *Proc. Nat'l Acad. Sci. USA* (1988) 85: 7177–81.

Wang, *Ann. Rev. Bochem.* (1996) 65: 635–692.

Watt and Hickson, *Bioche. J.* (1994) 303: 681–695.

Wigley *Ann. Rev. Biophys. Biomolec. Struct.* (1995) 24: 185–208.

Reaction components:

Epitope-tagged DNA Topoisomerase IV (via ParC subunit)

Double-stranded oligonucleotide substrate with 3'-Biotin

Measure enzyme activity by chemiluminescence

Reaction components:

Epitope-tagged DNA Topoisomerase IV (via ParC subunit )

DNA substrate: supercoiled plasmid DNA

Measure enzyme activity by chemiluminescence

HIGH-THROUGHPUT SCREENING ASSAYS FOR MODULATORS OF NUCLEIC ACID TOPOISOMERASES

FIELD OF THE INVENTION

The field of the invention relates to high-throughput assays for identifying modulators of topoisomerase activity. New solid and liquid phase assays are described, as are related compositions, apparatus and integrated systems.

BACKGROUND OF THE INVENTION

The great advances that have occurred in this century in treating infectious diseases are threatened by the emergence of strains of bacteria and other pathogens that are resistant to all currently known antibiotics. To counteract this threat, therapies that have novel mechanisms of action are needed.

One promising target for novel antipathogenic drugs is the topoisomerase family of enzymes. DNA topoisomerases play multiple roles in the maintenance and propagation of the genomes of both prokaryotes and eukaryotes. Thus, compounds that act as effective cellular inhibitors of topoisomerases are expected to act as cytotoxic agents through perturbation of the normal cell division process. Such agents that are sufficiently potent and selective will be of great use as antibacterial and antifungal pharmaceutical agents. Topoisomerases are also encoded by genomes of certain viruses, so development of topoisomerase inhibitors that are effective against viral topoisomerases may provide effective antiviral agents. In addition, because cell division is an important characteristic of cancers and other proliferative diseases, agents that inhibit topoisomerases will also find use as antineoplastic agents.

Topoisomerase inhibitors are classified into two general types. First, the class designated as "poisons" have in common the property of causing "trapping" of the target topoisomerase in the form of a covalent complex with the nucleic acid substrate. Second, the "non-poison" class inhibits the enzymatic activity of the topoisomerase without specific effects on steps of the catalytic cycle that involve formation or resolution of the enzyme-DNA covalent intermediate. Of the DNA topoisomerase inhibitors currently used as clinical antibiotic or antineoplastic agents, the "poisons" seem to be most effective, probably because such compounds result in the accumulation of irreversible genotoxic damage in target cells.

Shortcomings with previously available assays for topoisomerase inhibitors have hampered the search for novel topoisomerase inhibitors. For example, many previously available assays require the use of radioactive compounds and/or suffer from a lack of sensitivity. Also, previously available topoisomerase inhibitor assays are not always amenable to high throughput screening methods such as are needed to screen large libraries or groups of potential inhibitors. Thus, a need exists for new assay methods for identifying topoisomerase inhibitors. The present invention meets this and other needs.

SUMMARY OF THE INVENTION

High throughput assays for screening of nucleic acid topoisomerase modulators are provided. Inhibitors and activators of topoisomerase activity can both be screened using the assays. Solid and liquid phase high throughput assays are provided, as are related assay compositions, integrated systems for assay screening and other features which will be evident upon review.

In one aspect, high-throughput solid phase assays are provided. In a first embodiment of the solid phase formats, a test mixture that contains a topoisomerase, an oligonucleotide substrate for the topoisomerase, and a potential activity modulator are incubated under conditions suitable for topoisomerase activity. The nucleic acid is bound to a solid support. A denaturant is added to the reaction mixture, which stabilizes any topoisomerase-nucleic acid complexes that are formed due to the presence of the activity modulator. The solid support is washed in a high salt solution, after which the presence or absence of immobilized topoisomerase-nucleic acid complexes is determined by contacting the solid support with a labeling agent that binds to the topoisomerase.

In a second aspect of the solid phase assays, a plasmid is used as the substrate for the topoisomerase. This embodiment involves incubating a test mixture that includes a topoisomerase, a nucleic acid, and a potential activity modulator under conditions suitable for topoisomerase activity. A denaturant is added to the test mixture, as is a moiety that binds to a solid support, and also to the topoisomerase. The solid support is washed in a high salt solution to remove nucleic acid which is not bound to the immobilization moiety. The solid support-bound immobilization moiety is contacted with a labeling agent that binds to the nucleic acid to allow detection of the presence or absence of a topoisomerase-nucleic acid complex on the solid support.

The invention also provides high-throughput liquid phase assays for identification of topoisomerase activity modulators. These assays involve incubating a test mixture that contains a topoisomerase, a nucleic acid comprising a first label and a second label, and a potential activity modulator, under conditions suitable for topoisomerase activity. The presence or absence of a detectable emission, e.g., an emission by the first label, an emission by the second label, and an emission resulting from a combination of the first and second label is detected. The presence or absence of the detectable emission indicates whether the first and second labels remain in close proximity to each other.

Kits, compositions and integrated systems for performing the assays are also provided.

DETAILED DESCRIPTION

Figure 1:
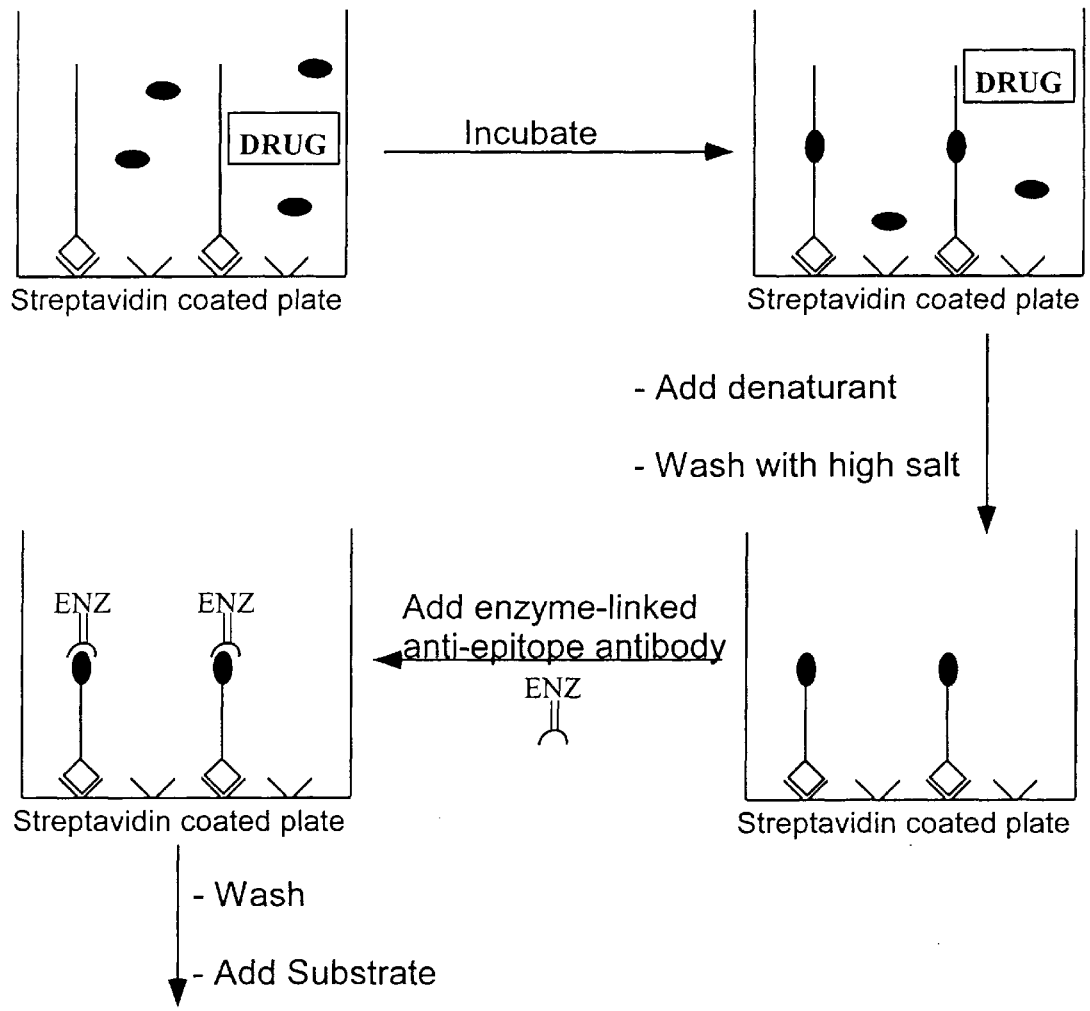
FIG. 1 shows a schematic diagram of the HTS assay for bacterial DNA topoisomerase I in the oligonucleotide substrate format. Representative data obtained using *E. Coli* DNA topoisomerase I in this assay format are shown in FIG. 5.

The invention provides both solid phase and liquid phase assay formats for measuring the activity of a topoisomerase in the presence of a potential topoisomerase activity modulator. High-throughput screening (HTS) methods, compositions, kits and integrated systems for performing the assays are also provided. In general, the assays are performed by contacting a nucleic acid with a topoisomerase in an appropriate reaction mixture that also includes a potential modulator of topoisomerase activity. If the potential topoisomerase activity modulator is a member of a class of topoisomerase inhibitors termed "poisons," a covalently linked complex between the topoisomerase and the nucleic acid substrate is trapped. This covalently linked complex is formed as an intermediate during all known nucleic acid topoisomerase reactions. In the assays of the invention, a denaturant is added to the reaction mixture, resulting in the stabilization of any covalent complexes that are present. The presence or absence of topoisomerase-nucleic acid complex is then detected to ascertain whether a modulator of topoisomerase activity was present in the reaction mixture.

For each of the assay formats described, 'no drug' control reactions which do not include a topoisomerase modulator provide a background level of covalent complex formation between the topoisomerase protein and the nucleic acid substrate (i.e., as formed upon addition of the denaturant) which is reflective of the overall topoisomerase activity of the enzyme at the time of denaturant addition. Hence, these assays are useful for detecting topoisomerase enzyme inhibitors of the "non-poison" class. Such inhibitors are also of potential as antibacterial, antifungal, antiviral and antineoplastic agents; see, for example Drlica et al. (1997) Microbiol. Mol. Biol. Rev. 61:377–392; Wang (1996) Ann. Rev. Biochem. 65:635–692; Froelich-Ammon et al. (1995) J Biol. Chem. 270:21429–21432; Roca et al. (1994) Proc Nati. Acad. Sci. U.S.A. 91:1781–1785; Maxwell (1993) Mol. Microbiol. 9:681–686; Sorensen et al. (1992) J. Mol. Biol. 228:778–786; Reece et al. (1991) Crit. Rev. Biochem. Mol. Biol. 26:335–375.

Topoisomerase modulators identified by use of the assays have value for in vitro modification of topoisomerase activity, e.g., as tools for recombinant methods, cell culture modulators, and the like. More importantly, these modulators provide lead compounds for drug development for a variety of conditions, including antibacterial, antifungal, antiviral or antineoplastic agents. Accordingly, the assays are of immediate value for their ability to identify lead compounds for pharmaceutical or other applications.

Indeed, because topoisomerases play a central role in nucleic acid metabolism and thus are important in a variety of biological processes relating to cell division, DNA replication, chromosome structure (condensation, segregation, and partition) and gene expression, modulators identified by the assays of the invention are leads for a variety of conditions, including neoplasia, viral infection, bacterial infection, fungal infection, and the like. In addition, topoisomerase modulators which specifically target undesired organisms, such as viruses, fungi, agricultural pests, or the like, can serve as fungicides, bactericides, herbicides, insecticides, etc. Thus, the range of conditions that topoisomerase activity modulators are applicable to includes conditions in humans and other animals, and in plants, e.g., for agricultural applications.

The invention represents an improvement over existing technology in several ways. For example, (a) there is no requirement that radioactive reagents be employed (although they are optionally used as discussed below); (b) the signal generated by the assay is significantly larger and more robust than those typically obtained using previously known topoisomerase assay methodologies; (c) a positive signal is generated by the presence of an inhibitor, thus facilitating the identification of specific inhibitory agents; (d) through use of different nucleic acid substrates, one can adapt the assays of the invention to screen for inhibitors of numerous different classes of topoisomerase enzymes, including those that may demonstrate sequence-specific nucleic acid binding properties; (e) one can assay multiple different topoisomerase enzymes in a single reaction, thus enhancing assay throughput; (f) the assays can be run in a parallel fashion such that multiple different topoisomerase enzymes are assayed simultaneously; (g) the assay format does not require that the enzyme be immobilized on a solid support during the course of the assay; (h) assays can be performed in the liquid or solid-phase; and (i) each of the formats described is readily amenable for automation and high throughput screening ("HTS") using current reagents, devices and methodologies.

Further in this regard, several aspects of the discovery were surprising. First, the assays are extremely sensitive relative to previously described assay formats, and only minimal quantities of the necessary reagents are required. Typically, the enzyme is present in a range of about 1–100 nM, so in cases in which topoisomerase availability is limiting, these assay formats have a significant advantage over previously known topoisomcrase assays. Second, prior to development of the assays described herein, one could not have predicted that topoisomerase enzymes (in particular, Type II topoisomerases) would effectively cleave oligonucleotides that are sufficiently short in length so as to make the assay formats economically viable. Third, the assays involve the use of a protein denaturant to ensure that covalent complexes formed between the enzyme and the nucleic acid substrate in the presence of topoisomerase inhibitors are maintained, rather than reversed, during the product detection phase of the assay. The absence of adverse effects by the denaturant on the subsequent steps of the assay was a surprising result of assay development.

Topoisomerases

The assays are useful for identifying modulators of many different topoisomerases. Topoisomerases are reviewed in, for example, Wigley, D. B. (1995) *Ann. Rev. Biophys. Biomolec. Struct.* 24: 185–208. The assay methods are useful for identifying activity modulators of, for example, Type I DNA topoisomerases (EC 5.99.1.2; also known as relaxing enzyme, untwisting enzyme, swivelase, nicking-closing enzyme, and omega-protein). The Type I DNA topoisomerases can convert one topological isomer of DNA into another, e.g. these topoisomerases can relax superhelical turns in DNA, interconvert simple and knotted rings of single-stranded DNA, and intertwist of single-stranded rings of complementary sequences. Type I topoisomerases act by catalyzing the transient breakage of DNA, one strand at a time, and the subsequent rejoining of the strands. In the process of breaking the strand, a Type I topoisomerase simultaneously forms a topoisomerase-DNA link in which the hydroxyl group of a tyrosine residue is joined to a 5'-phosphate on DNA, at one end of the enzyme-severed DNA strand. Sources of Type I topoisomerases include both prokaryotes and eukaryotes; examples of Type I topoisomerases include bacterial topoisomerases I and III, fungal topoisomerases I and III, human topoisomerases I, IIIα and IIIβ, as well as Type I viral topoisomerases. Some Type I topoisomerases are commercially available (e.g., calf thymus topoisomerase I, *Drosophila melanogaster* topoisomerase I, human topoisomerase I, and vaccinia topoisomerase I).

The assays are also applicable to modulators of Type II DNA topoisomerases (EC 5.99.1.3; also known as DNA topoisomerase II and DNA gyrase). The Type II DNA topoisomerases can change the topology of double-stranded DNA molecules, causing, for example, the relaxation of supercoiled DNA molecules, catenation, decatenation, knotting and unknotting of circular DNA (for review, see Watt and Hickson (1994) *Biochem. J.* 303:681–695). Type II topoisomerases act by a concerted breakage and reunion activity involving both strands of the DNA duplex. This activity is absolutely required for DNA replication and transcription. The active species of bacterial type II topoisomerases is a heterotetramer consisting of, for the DNA gyrases, two "A" (or "α") subunits and two "B" (or "β") subunits (Tsai-Pflugfelder et al. (1988) *Proc. Nat'l. Acad. Sci. USA* 85: 7177–81; Jenkins et al. (1992) *Nucleic Acids Res.* 20:5587–92), commonly referred to as GyrA and GyrB, respectively. Topoisomerase IV, which is a type II topoisomerase found in bacteria, comprises two subunits, ParC and ParE. The ParC subunit is homologous to the gyrase A protein, while the ParE subunit is homologous to the gyrase B subunit (Kato et al. (1990) *Cell* 63: 393–404; published erratum appears in *Cell* (1991) 65:1289). The GyrA or ParC subunit catalyzes breaking and rejoining of the DNA strands, while the GyrB or ParE subunit catalyzes ATP hydrolysis. Examples of Type II topoisomerases include, for example, bacterial topoisomerases II and IV, fungal topoisomerase II, human topoisomerases IIα and IIβ as well as Type II viral topoisomerases.

Other types of topoisomerases can also be used in the assays of the invention. For example, a CDNA encoding human DNA topoisomerase III (Hanai et al. (1996) *Proc. Nat. Acad. Sci.* 93: 3653–3657) has been cloned and sequenced; the gene encoding this topoisomerase is commonly deleted in patients with the Smith-Magenis syndrome (Elsea et al. (1998) *Am. J Med. Genet.* 75: 104–108. DNA topoisomerase III protein is homologous to the *E. coli* DNA topoisomerase I subfamily of enzymes, but shares no significant sequence homology with eukaryotic DNA topoisomerase I. Topoisomerase III catalyzes the reduction of supercoils in highly negatively supercoiled DNA.

In the assays of the invention, preferred topoisomerases are typically selected from medically relevant sources such as human topoisomerases I, IIα, IIβ, IIIα, and IIIβ (e.g., for assays designed to identify compounds which modulate cell growth, e.g., for inhibition of neoplasia); or from infectious organisms such as infectious fungi, e.g., Aspergillus, Candida species; bacteria, particularly *E. coli*, which serves a model for pathogenic bacteria, as well as medically important bacteria such as Staphylococci (e.g., *aureus*), Streptococci (e.g. *pneumoniae*), Clostridia (e.g., *perfringens*), Neisseria (e.g., *gonorrhoea*), Enterobacteriaceae (e.g., *coli*), Helicobacter (e.g., *pylori*), Vibrio (e.g., *cholerae*), Capylobacter (e.g., *jejuni*), Pseudomonas (e.g., *aeruginosa*), Haemophilus (e.g., *influenzae*), Bordetella (e.g., *pertussis*), Mycoplasma (e.g., *pneumoniae*), Ureaplasma (e.g., *urealyticum*), Legionella (e.g., *pneumophila*), Spirochetes (e.g., *Treponema, Leptospira* and *Borrelia*), Mycobacteria (e.g., *tuberculosis, smegmatis*), Actinomyces (e.g., *israelii*), Nocardia (e.g., *asteroides*), Chlamydia (e.g., *trachomatis*), Rickettsia, Coxiella, Ehrilichia, Rochalimaea, Brucella, Yersinia, Fracisella, and Pasteurella; protozoa such as sporozoa (e.g., Plasmodia), *rhizopods* (e.g., Entamoeba) and flagellates (Trypanosoma, Leishmania, Trichomonas Giardia, etc.); viruses such as the (+) RNA Poxviruses (e.g., *vaccinia*) viruses and certain dsDNA viruses (e.g., African Swine Fever Virus). Other assays are designed to be relevant to non-medical uses, such as assays for inhibitors of topoisomerases from crop pests e.g., insects, fungi, weed plants, and the like. Preferred topoisomerases include human topoisomerases I, IIα, IIβ, IIIα, and IIIβ and bacterial topoisomerases I, II, III and IV.

Topoisomerases may be purified from a natural source or may be recombinantly produced, and are usually provided in at least a partially-purified form, although the assays can function when provided with a crude cell lysate that contains a topoisomerase. In a preferred embodiment, the topoisomerases are synthesized using recombinant DNA methodology. Generally this involves creating a DNA sequence that encodes the topoisomerase, modified as desired, placing the DNA in an expression cassette under the control of a particular promoter, expressing the protein in a host, isolating the expressed protein and, if required, renaturing the protein. Topoisomerase nucleic acids that are useful for recombinant production of topoisomerases for use in the assays of the invention, and methods of obtaining such nucleic acids, are known to those of skill in the art. Topoisomerase nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), the selfsustained sequence replication system (SSR). Primers suitable for amplification and cloning of Type II topoisomerases are described in, for example, U.S. Pat. No. 5,645,994. A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Researchs* (1991) 3: 81–94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science*, 241: 1077–1080; Van Brunt (1990) *Biotechnology*, 8: 291–294; Wu and Wallace, (1989) *Gene*, 4: 560; and Barringer et al. (1990) *Gene*, 89: 117.

DNA encoding the topoisomerases can be prepared by any suitable method as described above, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.*, 22: 1859–1862; and the solid support method of U.S. Pat. No. 4,458,066. In one preferred embodiment, a nucleic acid encoding a topoisomerase can be isolated by routine cloning methods. A nucleotide sequence of a topoisomerase gene as provided in, for example, GenBank or other sequence database can be used to provide probes that specifically hybridize to a topoisomerase gene in a genomic DNA sample, or to a topoisomerase mRNA in a total RNA sample (e.g., in a Southern or Northern blot). Once the target topoisomerase nucleic acid is identified, it can be isolated according to standard methods known to those of skill in the art (see, e.g., Sambrook et al. (1989) *Molecular Cloning: A Laboratory Manual*, 2nd Ed., Vols. 1–3, Cold Spring Harbor Laboratory; Berger and Kimmel (1987) *Methods in Enzymology*, Vol. 152: *Guide to Molecular Cloning Techniques*, San Diego: Academic Press, Inc.; or Ausubel et al. (1987) *Current Protocols in Molecular Biology*, Greene Publishing and Wiley-Interscience, New York).

Topoisomerases can be expressed in a variety of host cells, including *E. coli*, other bacterial hosts, yeast, and various higher eukaryotic cells such as the COS, CHO and HeLa cells lines and myeloma cell lines. Examples of useful bacteria include, but are not limited to, Escherichia, Enterobacter, Azotobacter, Erwinia, Bacillus, Pseudomonas, Klebsielia, Proteus, Salmonella, Serratia, Shigella, Rhizobia, Vilreoscilla, and Paracoccus. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids encoding topoisomerases can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant topoisomerases can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology* Vol. 182: *Guide to Protein Purification.*, Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

Occasionally only a portion of a native topoisomerase is used in the assay, the portion being sufficient for topoisomerase activity of preferably not less than an order of magnitude less than that of the full-length topoisomerase. Portions capable of imparting the requisite binding specificity and affinity are readily identified by those skilled in the art. A wide variety of molecular and biochemical methods are available for generating catalytic fragments of a topoisomerase.

Reaction mixtures for the assays are such that topoisomerases are catalytically active. Prokaryotic type I topoisomerases require $Mg^{2+}$ (generally 1–5 mM $MgCl_2$), while eukaryotic type I topoisomerases generally do not require $Mg^{2+}$. Type I topoisomerases do not require any high energy cofactor, while some reactions of Type II topoisomerases utilize ATP. Topoisomerases are active across a relatively broad pH range, with an optimum in conventional Tris buffers of 7.6 for Type I topoisomerases and 7.5–9.0 in Type II topoisomerases. Reactions can also include one or more of a reducing agent (e.g., 2–5 mM dithiothreitol), a condensing agent (e.g., 5 mM spermidine), and an inert enzyme stabilizer (e.g., BSA).

Solid Phase Assays

In the solid phase assays of the invention, an effect of a potential topoisomerase activity modulator on the activity of a DNA topoisomerase is determined by detecting the presence of a covalent linkage between the topoisomerase and a substrate nucleic acid. The covalent complex is immobilized prior to detection. Two general types of solid phase topoisomerase modulation assays are provided by the invention, one of which uses an oligonucleotide substrate and the other of which uses a plasmid substrate.

Assays Employing Oligonucleotide Substrates

A first embodiment of the solid phase topoisomerase assay involves the use of an oligonucleotide as the substrate for the topoisomerase. A test reaction mixture which includes a topoisomerase, a tagged nucleic acid comprising a tag, and a potential activity modulator is incubated for a suitable period of time under conditions appropriate for topoisomerase activity. A denaturant is added to the test mixture, which stabilizes the covalent topoisomerase-oligonucleotide complex that is trapped when a topoisomerase inhibitor of the "poison" class is present. A solid support is also provided, to which the tag is bound either before or after the addition of the denaturant, thus binding the tagged nucleic acid to the solid support. The solid support is then washed in a high salt solution, and the solid support-bound tagged nucleic acid is contacted with a labeling moiety that binds to the topoisomerase. By detecting the presence or absence of the labeling moiety on the solid support, one can determine whether the potential activity modulator has had an effect on topoisomerase activity.

The assays make use of a protein denaturant to stabilize the covalent linkage of topoisomerase and tagged nucleic acid. Suitable denaturants include, for example sodium dodecyl sulfate at a concentration of between about 0.05% and 0.5%, more preferably the concentration of denaturant is between about 0.2 and 0.5 percent.

Nucleic acids used in this type of assay format can be any polynucleotide that is a substrate for a topoisomerase. Such polynucleotides can include single-stranded RNA, a double-stranded RNA, a single-stranded DNA, a double-stranded DNA, a double-stranded DNA-RNA hybrid, an RNA analogue, and a DNA analogue. The particular topoisomerase being assayed can influence the choice of substrate oligonucleotide. For example, a Type II topoisomerase requires a double-stranded oligonucleotide target, while a Type I topoisomerase can use either single- or double-stranded nucleic acids as a substrate. The tagged nucleic acid is covalently or non-covalently attached to a tag (including the case noted below in which the tag is simply a terminal nucleotide on the nucleic acid).

Most commonly, this assay format uses oligonucleotides which are made synthetically. Synthetic oligonucleotides are typically synthesized chemically according to common solid phase phosphoramidite triester methods described, e.g., by Beaucage and Caruthers (1981) *Tetrahedron Letts.* 22(20) :1859–1862, e.g., using an automated synthesizer, as described in Ncedham-VanDevanter et al. (1984) *Nucleic Acids Res.* 12: 6159–6168. Oligonucleotides can also be custom made and ordered from a variety of commercial sources known to persons of skill. In other embodiments, the nucleic acids are made recombinantly according to standard techniques, described, e.g., in Berger, Sambrook and Ausubel, supra.

It is a discovery of this invention that topoisomerase enzymes typically need only small nucleic acid substrates for activity. For an assay of a bacterial Type I topoisomerase, the oligonucleotide substrate is typically at least about 11 nucleotides in length, with oligonucleotides that are at least about 20 nucleotides preferred. Generally, the oligonucleotide targets for bacterial Type I topoisomerases are about 50 nucleotides or less in length. A preferred range for Type I topoisomerase substrates is between about 10 and about 50 nucleotides, and most preferably the substrates are between about 25 and about 45 nucleotides in length. Bacterial Type II topoisomerase assays typically require an oligonucleotide substrate that is at least about 20 nucleotides in length, more preferably the substrate is at least about 40 nucleotides, and most preferably is about 45 nucleotides in length. The lower and upper size limits for Type II topoisomerase substrates is often dependent upon the particular topoisomerase. The design of oligonucleotide substrates for utilization in assays of eukaryotic topoisomerase enzymes is guided by the nature of the target enzyme as determined empirically and/or by reference to published information (see, Wang (1996) *Ann. Rev. Biochem.* 65:635–692 and references cited therein).

For many applications, random nucleotide sequences are suitable for use as substrates in the topoisomerase assays of the invention. In certain embodiments, however, it is desirable to include within the substrate oligonucleotide a sequence that is preferred for binding of a topoisomerase of interest. For example, substrates bearing preferred binding sites for the bacterial topoisomerase II enzyme (DNA gyrase) can be designed to incorporate the high affinity binding and cleavage sites identified, for example, in the *E. coli* chromosome (Franco et al. (1988) *J. Mol. Biol.* 201: 229–233; Condemmie et al. (1990) *Nucleic Acids Res.* 18: 7389–7397), bacteriophage Mu (Pato et al. (1990) *Proc. Natl. Acad. Sci. U.S.A* 87: 8716–8720), or plasmids pSC101 (Miller et al. (1990) *Cell* 62: 127–133) or pBR322 (Fisher et al. (1981) *Proc. Natl. Acad. Sci. U.S.A* 78: 4165; Morrison et al. (1981) *Proc. Natl. Acad. Sci. U.S.A* 78:1981; Kirkegaard et al. (1981) *Cell* 23: 721; Lockshon et al. (1985) *J Mol. Biol.* 181: 63; O'Connor et al. (1985) *J. Mol. Biol.* 181: 545). Similarly, as will be appreciated by those skilled in the art, the design of oligonucleotide or plasmid (see section 'Assays employing plasmid substrates') substrates for other nucleic acid topoisomerases can be designed by reference to empirically obtained or published data on experiments relating to the characterization of the sequence preferences for the target enzyme in nucleic acid binding and cleavage.

Short oligonucleotides (as opposed to longer nucleic acids) are preferred substrates for the topoisomerase assays because they can be made synthetically, because hybridization and washing in the assays leads to lower background levels and because they can be synthesized directly on the solid phase, if desired.

The oligonucleotide substrates used in the assays typically include a tag by which the oligonucleotides can be attached to a solid support. Generally, the tag is present at one end of the oligonucleotide. Where the topoisomerase of interest becomes attached to a 5' phosphate of one of the nucleotides in the target, the tag is preferably attached to the 3' end of the oligonucleotide. Conversely, the tag is preferably attached to the 5' end of a substrate oligonucleotide for a topoisomerase of interest that forms a covalent linkage to a 3' phosphate. The presence of a topoisomerase inhibitor in the reaction mixture stabilizes the covalently linked topoisomerase-nucleic acid complex that arises as an intermediate in the topoisomerase reaction; this complex is then trapped by addition of a denaturant to the reaction mixture. The tag thus functions to immobilize the nucleic acid-topoisomerase complex to a solid support. The immobilization of the oligonucleotide substrate can occur either prior to, simultaneously with, or after the addition of the denaturant to the reaction mixture.

The tag can be any of a variety of components. In general, a molecule which binds the tag (a tag binder) is fixed to a solid support, and the tagged DNA is attached to the solid support by interaction of the tag and the tag binder. A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. See, id. Indeed, the antibody can be either the tag or the tag binder, or antibodies can be used as both tags and tag binders. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as e.g., transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott and Power (1993) *The Adhesion Molecule FactsBook*, Academic Press New York, and Hulme (ed) *Receptor Ligand Interactions A Practical Approach*, Rickwood and Hames (series editors) Hulme (ed) IRL Press at Oxford Press N.Y.). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers such as heteropolymers in which a known drug is covalently bound to any of the above, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Specific tag-tag binder interactions occur when the tag and tag binder bind with a KD of at least about 0.01 $\mu$M, preferably at least about 0.001 $\mu$M or better, and most typically and preferably, 0.0001 $\mu$M or better, under standard assay conditions.

Synthetic attachment of DNA or RNA nucleic acids to various appropriate tags is performed using available techniques. In one embodiment, linkers are added to the nucleic acid and attachment to the tag is performed through the linker. Common linkers include polypeptide sequences, such as poly gly sequences of between about 5 and 200 amino acids. In some embodiments, proline residues are incorporated into the linker to prevent the formation of significant secondary structural elements by the linker. Such flexible linkers are known to persons of skill in the art. For example, poly(ethylene glycol) linkers are available from Shearwater Polymers, Inc., Huntsville, Alabama. These linkers optionally have amide linkages, sulfhydryl linkages, or heterofunctional linkages.

Tag binders are fixed to solid substrates using any of a variety of methods currently available. Solid substrates are commonly derivitized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield (1963) *J. Am. Chem. Soc*. 85: 2149–2154 (describing solid phase synthesis of, e.g., peptides); Geysen et al. (1987) *J. Immun. Meth*. 102: 259–274 (describing synthesis of solid phase components on pins). See, Frank and Doring (1988) *Tetrahedron* 44: 6031–6040 (describing synthesis of various peptide sequences on cellulose disks); Fodor et al. (1991) *Science*, 251: 767–777; Sheldon et al. (1993) *Clinical Chemistry* 39(4): 718–719 and Kozal et al. (1996) *Nature Medicine* 2(7): 753–759 (all describing arrays of biopolymers fixed to solid substrates). Non-chemical approaches for fixing tag binders to substrates include other common methods, such as heat, cross-linking by UV radiation, and the like.

Similarly, the tagged nucleic acid may be directly attached to a solid substrate in the assays of the invention. In this embodiment, the terminal end of the tagged nucleic acid is, itself, the molecular tag. In this embodiment, tagged nucleic acids are fixed to or synthesized on a solid support. A solid support is a matrix of material in a substantially fixed arrangement. Exemplar solid supports include glasses, plastics, polymers, metals, metalloids, ceramics, organics, etc. For example, using chip masking technologies and photoprotective chemistry it is possible to generate arrays of nucleic acid probes. These arrays, which are known, e.g., as "DNA chips," can include millions of nucleic acid regions on a substrate having an area of about 1 cm$^2$ to several cm$^2$, thereby incorporating sets of from a few to millions of tagged nucleic acids. See, e.g., Fodor et al. (1991) *Science*, 251: 767–777; Sheldon et al. (1993) Clinical Chemistry 39(4): 718–719, and Kozal et al. (1996) *Nature Medicine* 2(7): 753–759.

Solid supports can be flat or planar, or can have substantially different conformations. For example, the substrate can exist as particles, beads, strands, precipitates, gels, sheets, tubing, spheres, containers, capillaries, pads, slices, films, plates, slides, etc. Magnetic beads or particles, such as magnetic latex beads and iron oxide particles, are examples of solid substrates that can be used in the methods of the invention. Magnetic particles are described in, for example, U.S. Pat. No. 4,672,040, and are commercially available from, for example, PerSeptive Biosystems, Inc. (Framingham Mass.), Ciba Coming (Medfield Mass.), Bangs Laboratories (Carmel Ind.), and BioQuest, Inc. (Atkinson N.H.).

Once the tagged nucleic acids and, if present, covalently linked topoisomerase-oligonucleotide complexes are fixed to the solid support, the support is washed to remove non-immobilized components. Wash conditions are selected so that tags remain bound to any tag binders, and any covalently bound topoisomerase remains bound to the oligonucleotide substrate. Preferably, a high salt wash is used, e.g., about 0.2 to 2 M NaCl or KCl. Suitable wash solutions include, for example, TBS-T buffer containing 1 M NaCl (see Examples). One or more washes can be employed; in preferred embodiments, washes are repeated until a signal to noise ratio of 2×10×(or higher) is achieved, i.e., until at least about 50–90% of the unattached topoisomerase is removed from the solid support, and often until at least 90–95% is removed. The determination of how much topoisomerase remains can be done by performing a calibration of the assay, by performing the topoisomerase assay in the absence of a modulator and then repeatedly washing the solid support to determine the amount bound to the support through the tag, and the number of washes required to remove unbound topoisomerase.

In a preferred aspect, a solid support-bound complex between tagged nucleic acid and topoisomerase is contacted with a labelling moiety that specifically binds to an epitope on the topoisomerase. The epitope can be an epitope that occurs naturally in the topoisomerase, in which case an example of a suitable binding agent is an antibody that binds to the topoisomerase. Alternatively, the epitope can be associated with component that is attached to the topoisomerase. For example, a tag selected from those discussed above as being suitable for attachment to the tagged nucleic acid can be attached to the topoisomerase. Preferably, the tag attached to the topoisomerase will be different than that attached to the tagged nucleic acid, so that the topoisomerase tag does not bind to the tag binder associated with the solid support. When a Type II topoisomerase is being used in the assays, the epitope is preferably associated with a subunit of the multi-subunit topoisomerase that becomes covalently attached to the tagged nucleic acid (i.e., a ParC subunit of Topoisomerase IV). If multiple topoisomerases are to be assayed in a single reaction, it is desirable to use a different epitope for each topoisomerase, thus allowing detection of each topoisomerase by use of a different label.

Appropriate epitopes, and methods for their attachment to polypeptides, are known to those of skill in the art. In a preferred embodiment, a fusion protein is produced by recombinant methods. For example, a polynucleotide encoding the topoisomerase is operably linked to a polynucleotide that encodes an epitope for which convenient means of detection exist. The polynucleotide encoding the epitope is preferably placed at a location relative to the topoisomerase gene that does not disrupt the topoisomerase activity of the fusion protein. Methods for constructing and expressing genes that encode fusion proteins are well known to those of skill in the art. Examples of these techniques and instructions sufficient to direct persons of skill through many cloning exercises are found in Berger, Sambrook, and Ausubel, supra. Examples of suitable epitopes include the myc and V-5 reporter genes; expression vectors useful for recombinant production of topoisomerases having these epitopes are commercially available (e.g., Invitrogen (Carlsbad Calif.) vectors pcDNA3.1/Myc-His and pcDNA3.1/V5-His are suitable for expression in mammalian cells). Additional expression vectors for suitable fusion proteins, and corresponding detection systems are known to those of skill in the art, and several are commercially available (e.g., FLAG™ (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In *Genetic Engineering: Principles and Methods*, J. K. Setlow, Ed., Plenum Press, N.Y.; commercially available from Qiagen (Santa Clarita, Calif.)).

The labels used in the assays of invention can be primary labels (where the label comprises an element which is detected directly) or secondary labels (where the detected label binds to a primary label, e.g., as is common in immunological labeling). An introduction to labels, labeling procedures and detection of labels is found in Polak and Van Noorden (1997) *Introduction to Immunocytochemistry*, second edition, Springer Verlag, N.Y. and in Haugland (1996) *Handbook of Fluorescent Probes and Research Chemicals*, a combined handbook and catalogue Published by Molecular Probes, Inc., Eugene, OR. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetramethylrhodamine isothiocyanate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse-radish peroxidase, alkaline phosphatase etc.) spectral colorimetric labels such as colloidal gold or colored glass or plastic (e.g. polystyrene, polypropylene, latex, etc.) beads. The label may be coupled directly or indirectly to a component of the detection assay (e.g., the labeling nucleic acid) according to methods well known in the art. As indicated above, a wide variety of labels may be used, with the choice of label depending on sensitivity required, ease of conjugation with the compound, stability requirements, available instrumentation, and disposal provisions. In general, a detector which monitors a probe-target nucleic acid hybridization is adapted to the particular label which is used. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling nucleic acids is digitized for subsequent computer analysis.

Preferred labels include those which utilize 1) chemiluminescence (using Horseradish Peroxidase and/or Alkaline Phosphatase with substrates that produce photons as breakdown products) with kits being available, e.g., from Molecular Probes, Amersham, Boehringer-Mannheim, and Life Technologies/Gibco BRL; 2) color production (using both Horseradish Peroxidase and/or Alkaline Phosphatase with substrates that produce a colored precipitate) (kits available from Life Technologies/Gibco BRL, and Boehringer-Mannheim); 3) hemifluorescence using, e.g., Alkaline Phosphatase and the substrate AttoPhos (Amersham) or other substrates that produce fluorescent products, 4) Fluorescence (e.g., using Cy-5 (Amersham), fluorescein, and other fluorescent tags); 5) radioactivity using kinase enzymes or other end-labeling approaches, nick translation, random priming, or PCR to incorporate radioactive molecules into the labeling nucleic acid. Other methods for labeling and detection will be readily apparent to one skilled in the art.

Fluorescent labels are highly preferred labels, having the advantage of requiring fewer precautions in handling, and being amendable to high-throughput visualization techniques (optical analysis including digitization of the image for analysis in an integrated system comprising a computer). Preferred labels arc typically characterized by one or more of the following: high sensitivity, high stability, low background, low environmental sensitivity and high specificity in labeling. Fluorescent moieties, which are incorporated into the labels of the invention, are generally are known, including Texas red, dixogenin, biotin, 1- and 2-aminonaphthalene, p,p'- diaminostilbenes, pyrenes, quaternary phenanthridine salts, 9-aminoacridines, p,p'- diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes, flavin and many others. Many fluorescent tags are commercially available from the SIGMA chemical company (Saint Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka ChemicaBiochemika Analytika (Fluka Chemie AG, Buchs, Switzerland), and Applied Biosystems (Foster City, Calif.), as well as many other commercial sources known to one of skill.

Most typically, topoisomerase inhibition is measured by quantitating the amount of label fixed to the solid support by the capture of the covalently linked complex between oligonucleotide and topoisomerase that occurs in the presence of an agent that inhibits topoisomerase activity. Typically, the presence in the reaction mixture of a modulator that inhibits topoisomerase activity will increase or decrease the amount of label fixed to the solid support relative to a control reaction which does not comprise the modulator, or as compared to a baseline established for a particular lot of topoisomerase. Means of detecting and quantitating labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems which are widely available.

Model Solid Phase Oligonucleotide-based Assays

The solid phase oligonucleotide-based assays of the invention are further illustrated by consideration of the attached figures. These assays are provided by way of illustration and not by way of limitation; one of skill will recognize a variety of substitutions that can be made upon complete review of this disclosure.

FIG. 1 depicts a preferred exemplar assay of the invention. A tagged DNA having a biotin tag attached to its 3' end is fixed to a streptavidin or neutravidin coated plate by attachment to the biotin tag. A bacterial Type I topoisomerase that includes a detectable epitope is incubated with the oligonucleotide substrate in a reaction mixture suitable for topoisomerase activity. The presence of a topoisomerase inhibitor ("DRUG" in FIG. 1) in the reaction mixture results in trapping of the intermediate complex that forms as a result of a covalent linkage between topoisomerase and oligonucleotide. A denaturant is added to stabilize the intermediate, after which the support is washed in a high salt solution. A labeled antibody that binds to the topoisomerase epitope is then placed in contact with the solid support. The amount of enzyme activity is measured by chemiluminescence, preferably after washing to remove any unbound antibody from the solid support.

Figure 2:
FIG. 2 shows a schematic diagram of the HTS assay for bacterial DNA topoisomerase IV in the oligonucleotide substrate format. Representative data obtained using *E. coli* DNA topoisomerase IV in the assay format are shown in FIG. 6.
Figure 2:
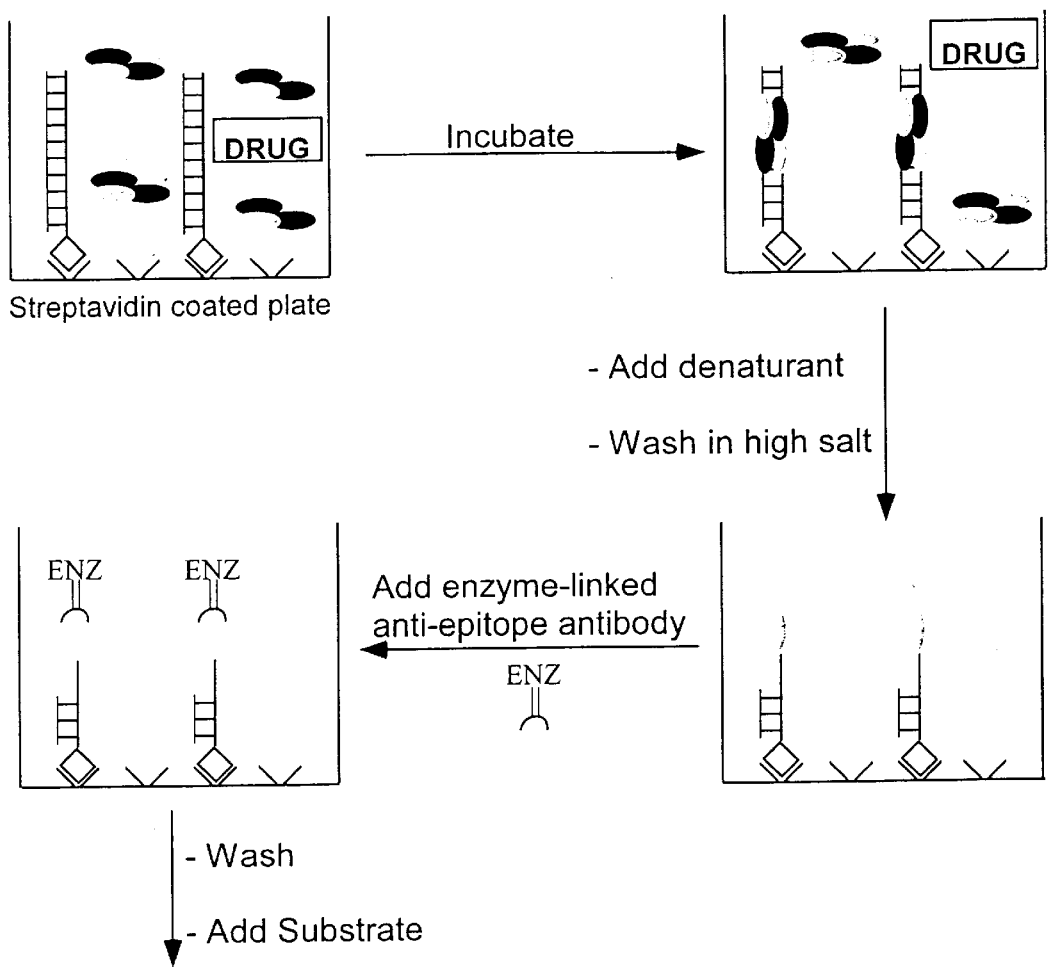

FIG. 2 depicts a second preferred exemplar assay of the invention. This assay is similar to that depicted in FIG. 1, except that a Type II topoisomerase is used, and the oligonucleotide substrate is double-stranded. Again, the oligonucleotide is immobilized on the solid support by binding the biotin tag attached to the 3' end of the nucleic acid to the streptavidin-coated plate. After incubation in the presence of a topoisomerase inhibitor ("DRUG" in the figure), the resulting covalent complex is stabilized by addition of a denaturant. After a high-salt wash, the presence or absence of topoisomerase bound to the solid support is detected through use of a labelling moiety that binds to the epitope on the topoisomerase.

Assays Employing Plasmid Substrates

In another embodiment, the invention provides methods of measuring the activity of a topoisomerase in the presence of a potential topoisomerase activity modulator by using a nucleic acid such as a plasmid as the substrate for the topoisomerase. These assays typically involve incubating a test mixture comprising: a topoisomerase comprising an epitope, a nucleic acid, and a potential activity modulator in suitable conditions for topoisomerase activity. A mild denaturant is added to the test mixture, which stabilizes the covalent linkage between topoisomerase and nucleic acid that is trapped when the activity modulator inhibits topoisomerase activity. The denaturant is added to the reaction mixture either prior to or simultaneously with the addition of an immobilization moiety which comprises a tag which binds to a solid support and a binding moiety that binds to the epitope on the topoisomerase. The tag is then bound to a solid support, thereby binding the immobilization moiety to the solid support. The solid support is washed in a high salt solution to remove nucleic acid which is not bound to the immobilization moiety. Next, the solid support-bound topoisomerase-nucleic acid complexes, if any are present, are contacted with a labeling moiety that includes a primary label and a binding moiety that binds to the nucleic acid. The activity of topoisomerase in the presence of the topoisomerase activity modulator is ascertained by determining whether the nucleic acid is bound to the immobilized topoisomerase by detecting the presence or absence of the labeling moiety on the solid support.

The nucleic acid substrates used in these assay formats are typically plasmids, although other nucleic acids are also suitable. The size of the nucleic acid substrate is typically less than about 20 kb, more preferably the substrates are about 10 kb or less in length, and most preferably the nucleic acid substrates are about 2.5 kb to about 4 kb. By changing the topological form of the substrates, one can adapt the assay to screen for inhibitors of numerous different classes of topoisomerase enzyme, including those that may demonstrate sequence-specific nucleic acid binding properties. Although linear nucleic acids can be used, a covalently closed circular nucleic acid is preferred for most topoisomerases. A particularly preferred substrate for some topoisomerases is a supercoiled plasmid. For Type I topoisomerases, the substrate nucleic acid can be either single- or double-stranded, while type II topoisomerases generally require a double-stranded nucleic acid.

The choice of a preferred plasmid substrate for use in this assay format can be made with reference to empirically obtained and/or published data relating to biochemical and enzymatic characterization of the target enzyme. In some cases, this involves consideration of the inclusion within the plasmid sequence utilized of any sequence for which the target enzyme is demonstrated to have a particular preference in the substrate binding or cleavage steps of the topoisomerase reaction. For example, preferred plasmids for the bacterial topoisomerase II enzyme (DNA gyrase) can incorporate the high affinity binding and cleavage sites identified in the *E. coli* chromosome (Franco et al. (1988) *J. Mol. Biol.* 201: 229–233; Condemmie et al. (1990) *Nucleic Acids Res.* 18: 7389–7397), bacteriophage Mu (Pato et al. (1990) *Proc. Natl. Acad. Sci. U.S.A* 87: 8716–8720), or plasmids pSC101 (Miller et al. (1990) *Cell* 62: 127–133) or pBR322 (Fisher et al. (1981) *Proc. Natl. Acad. Sci. U.S.A* 78: 4165; Morrison et al. (1981) *Proc. Natl. Acad. Sci. U.S.A* 78:1981; Kirkegaard et al. (1981) *Cell* 23: 721; Lockshon et al. (1985) *J Mol. Biol.* 181: 63;; O'Connor et al. (1985) *J Mol. Biol.* 181: 545). In addition, the topological state of the plasmid utilized in the assay is an important factor and in each case would be determined with reference to published data relating to biochemical and enzymatic characterization of the target enzyme. For example, negatively supercoiled closed circular plasmid substrates represent the preferred substrates for bacterial topoisomerases I and IV while a relaxed closed circular plasmid substrates may be optimal for bacterial topoisomerase II.

The reaction mixtures, denaturants, and wash solutions used in the oligonucleotide-based solid phase assays described above are suitable for the plasmid-based assays. In both cases, the reaction mixture contains any salts and/or ATP or other energy source, if either is required for the particular topoisomerase. The denaturant is added to the reaction mixture in an amount that stabilizes the covalent intermediate complex that is trapped in the presence of a topoisomerase inhibitor.

Immobilization of the topoisomerase-nucleic acid complex is achieved by virtue of an immobilization moiety that includes a tag that can bind to a solid support, and a second tag that can bind to an epitope on the topoisomerase. As is the case for the oligonucleotide-based assays described above, the epitope on the topoisomerase can be either a naturally occurring epitope, or can be one that is attached to the topoisomerase (e.g., by chemical linkage or by expression of a fusion protein in which the topoisomerase enzyme is linked to the epitope.

After washing the solid support to remove unbound material, the presence or absence of immobilized topoisomerase-nucleic acid complexes is detected by contacting the solid support with a labeling moiety. The labeling moiety includes a primary label (discussed above) linked to a binding moiety that can bind to the nucleic acid that is linked to the immobilized topoisomerase. Suitable binding moieties include, for example, polynucleotides that are complementary to either strand of the target nucleic acid. Such polynucleotides hybridize to the immobilized nucleic acid under suitable conditions that are known to those of skill in the art. Hybridization of the labeling moiety can result in formation of either a duplex or a triplex (in the case of a double-stranded target nucleic acid). Also suitable for use as binding moieties are anti-DNA polyclonal or monoclonal antibodies (for example, see sources listed in the appropriate section of MSRS Catalog of Primary Antibodies, R. V. Wiemer, Ed., Aerie (1995)). Nucleic acid stains can also be used to detect immobilized nucleic acids; such stains include, for example, cyanine dyes, phenanthridines and acridines, indoles and imidazoles, and the like (see, e.g., Haugland (1996) *Handbook of Fluorescent Probes and Research Chemicals, supra.*, Chapter 8). Alternatively, the target nucleic acids can be labeled prior to use in the assay, in which detection does not require the addition of an exogenous labeling moiety.

Detection and, if desired, quantitation of the amount of label fixed to the solid support by the capture of the covalently linked complex between oligonucleotide and topoisomerase can be performed as described above.

Model Solid Phase Plasmid-based Assays

Figure 3:
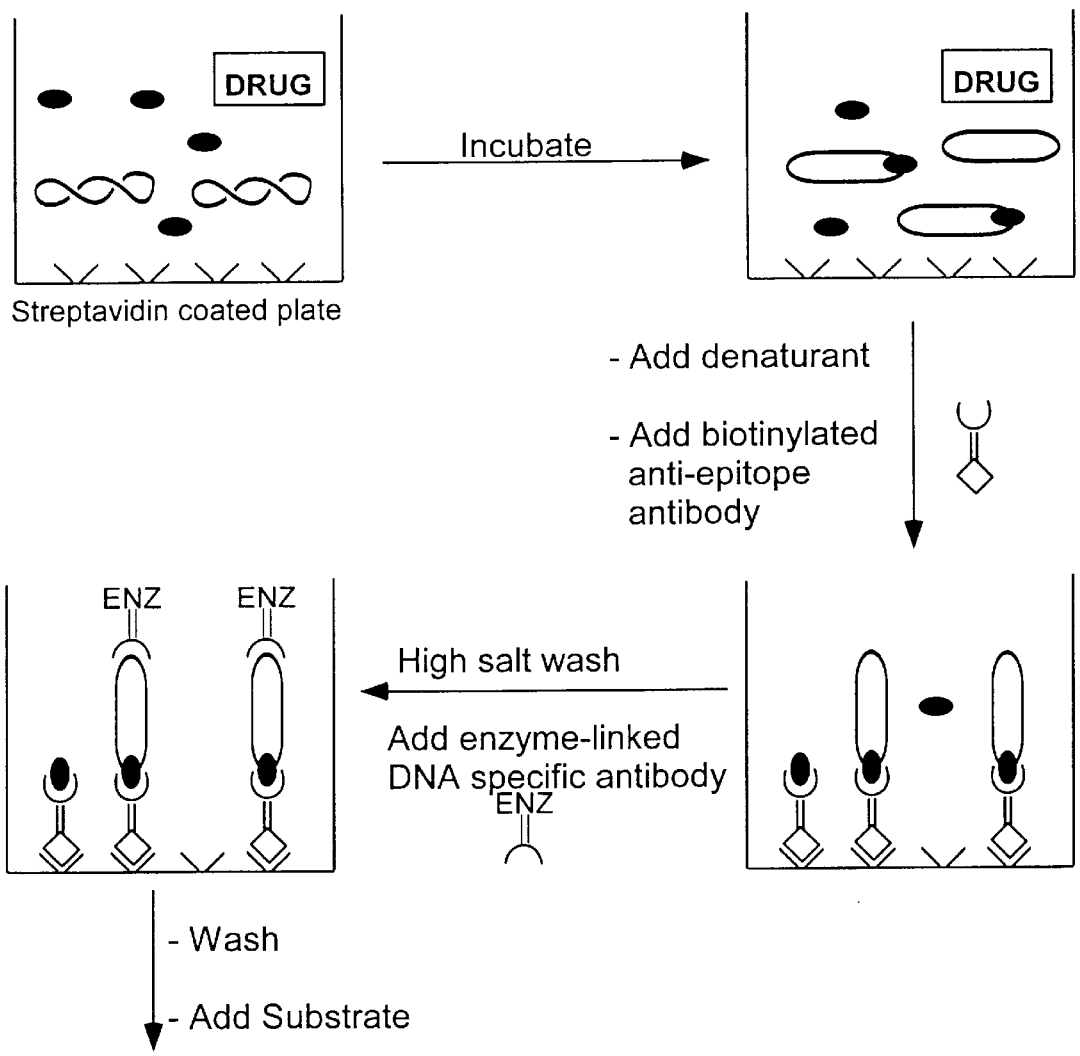
FIG. 3 provides a schematic diagram of the HTS assay for bacterial DNA topoisomerase I in a format utilizing a plasmid DNA substrate.

FIG. 3 depicts a preferred solid-phase assay format in which a supercoiled plasmid (either single- or double-stranded) is used as the substrate for the topoisomerase. In this embodiment, a bacterial Type I topoisomerase that is tagged with an epitope (Myc) is incubated for two hours at room temperature in a reaction mixture in the presence of the supercoiled plasmid DNA and a potential topoisomerase activity modulator ("DRUG" in FIG. 3). A mild detergent is added to the reaction mixture, which stabilizes any covalently linked plasmid-topoisomerase complexes that arise as a result of trapping of the reaction intermediate by the potential activity modulator. An immobilization moiety (in the depicted embodiment, a biotinylated anti-Myc antibody). If desired, the immobilization moiety can be added simultaneously with the denaturant. The immobilization moiety binds to the streptavidin-coated solid support, thus immobilizing the topoisomerase-plasmid complex, if present. After a high-salt wash, the presence of absence of the complex is detected by addition of a labelling moiety that binds to the plasmid (an enzyme-linked anti-DNA antibody, in the Figure). The support is then washed, after which substrate for the enzyme is added, and enzyme activity is measured by chemiluminescence. The label is then quantitated, thereby determining how much of the topoisomerase is bound to the plasmid DNA. The activity of a topoisomerase modulator ("DRUG" in FIG. 3) is measured by comparing the amount of bound topoisomerase-plasmid complex in the presence or absence of the modulator.

Figure 4:
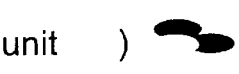
FIG. 4 shows a schematic diagram of the HTS assay for bacterial DNA topoisomerase IV in a format utilizing a plasmid DNA substrate. Representative data obtained using E. coli DNA topoisomerase II in this assay format are shown in FIG. 7.
Figure 4:
Figure 4:
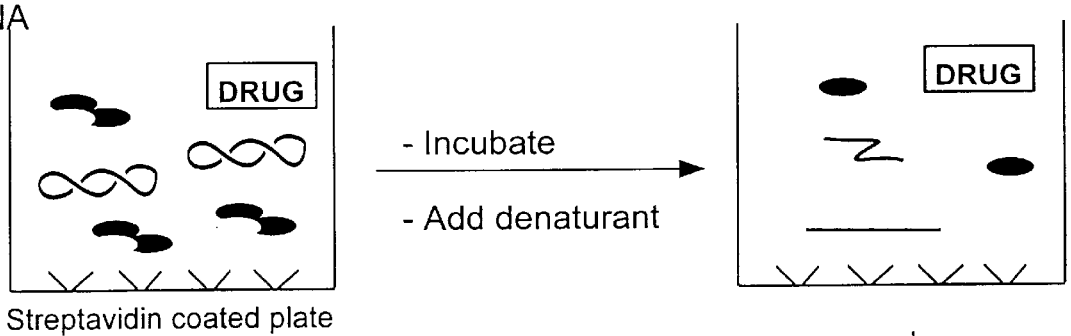
Figure 4:
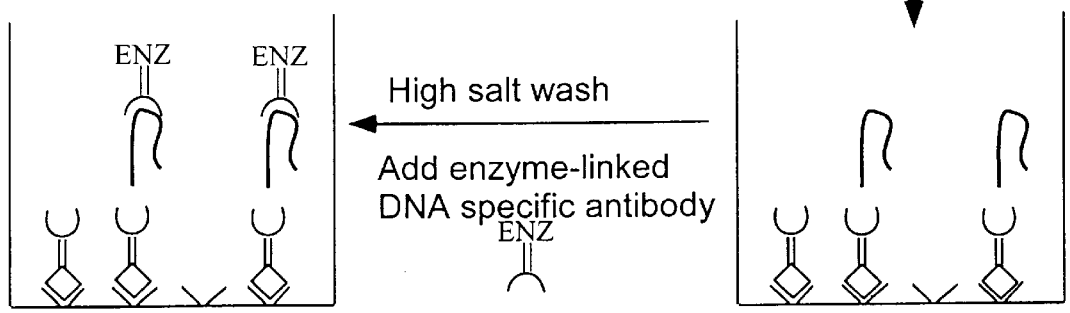

A second preferred plasmid-based assay system is shown in FIG. 4. In this case, inhibition of a Type II topoisomerase by a potential activity modulator is tested. The substrate supercoiled plasmid DNA is double-stranded in this assay. In other respects, the assay is carried out in a similar manner to that described above.

Liquid Phase Assays

The liquid phase assays of the invention provide methods of measuring the activity of nucleic acid topoisomerase in the presence of a potential topoisomerase activity modulator. In the methods, a test reaction mixture including the topoisomerase and a nucleic acid substrate is incubated in the liquid phase. Typically, the substrate nucleic acids have a first label and a second label. Most typically in the liquid phase assays of the invention, the first and second label interact when in proximity (e.g., due to resonance transfer), and the relative proximity of the first and second labels is determined by measuring a change in the intrinsic fluorescence of the first or second label. Commonly, the emission of the first label is quenched by proximity of the second label. After incubation, the presence or absence of a detectable label emission is detected. The detected emission can be any of: an emission by the first label, an emission by the second label, and an emission resulting from a combination of the first and second label. Typically, a change in the signal due to topoisomerase activity modulator-induced cleavage of the nucleic acid between the labels is detected (e.g., a reduction in quenching which leads to an increase in signal from either or both of the labels, a change in signal color, and the like).

Many appropriate interactive labels are known. For example, fluorescent labels, dyes, enzymatic labels, and antibody labels are all appropriate. Examples of preferred interactive fluorescent label pairs include terbium chelate and TRITC (tetramethylrhodamine isothiocyanate), europium cryptate and Allophycocyanin and many others known to one of skill. Similarly, two colorimetric labels can result in combinations which yield a third color, e.g., a blue emission in proximity to a yellow emission provides an observed green emission.

With regard to preferred fluorescent pairs, there are a number of fluorophores which are known to quench one another. Fluorescence quenching is a bimolecular process that reduces the fluorescence quantum yield, typically without changing the fluorescence emission spectrum. Quenching can result from transient excited state interactions, (collisional quenching) or, e.g., from the formation of non-fluorescent ground state species. Self quenching is the quenching of one fluorophore by another; it tends to occur when high concentrations, labeling densities, or proximity of labels occurs. Fluorescent resonance energy transfer (FRET) is a distance dependent excited state interaction in which emission of one fluorophore is coupled to the excitation of another which is in proximity (close enough for an observable change in emissions to occur). Some excited fluorophores interact to form excimers, which are excited state dimers that exhibit altered emission spectra (e.g., phospholipid analogs with pyrene sn-2 acyl chains); see, Haugland (1996) *Handbook of Fluorescent Probes and Research Chemicals*, Published by Molecular Probes, Inc., Eugene, OR., e.g., at chapter 13).

The Forster radius ($R_o$) is the distance between fluorescent pairs at which energy transfer is 50% efficient (i.e., at which 50% of excited donors are deactivated by FRET. The magnitude of $R_o$ is dependent on the spectral properties of donor and acceptor dyes:

$$R_o = [(8.8 \times 10^{23})(K^2)(n^{-4})(QY_D)(J)(\lambda)]^{1/6} \text{Å}$$

where:

$K^2$=dipole orientation range factor (range 0 to 4, $K^2 = 2/3$ for randomly oriented donors and acceptors);

$QY_D$ =fluorescence quantum yield of the donor in the absence of the acceptor;

n=refractive index; and, $J(\lambda)$=spectral overlap integral=$\int \epsilon_A(\lambda) \cdot F_D \lambda \cdot \lambda^4 d\lambda \cdot \text{cm}^3 \text{M}^{-1}$, Where $\epsilon_A$=extinction coefficient of acceptor and $F_D$=Fluorescence emission intensity of donor as a fraction of total integrated intensity.

| Donor | Acceptor | $R_o$ (Å) |
|---|---|---|
| Fluorescein | tetramethylrhodamine | 55 |
| IAEDANS | fluorescein | 46 |
| Fluorescein | Fluorescein | 44 |
| BODIPY | BODIPY | 57 |
| EDANS | DABCYL | 33 |

An extensive compilation of RP values are found in the literature; see, Haugland (1996) *Handbook of Fluorescent Probes and Research Chemicals* Published by Molecular Probes, Inc., Eugene, OR at page 46 and the references cited therein.

In most uses, the first and second labels are different, in which case FRET can be detected by the appearance of sensitized fluorescence of the acceptor or by quenching of the donor fluorescence. When the first and second labels are the same, FRET is detected by the resulting fluorescence depolarization.

In addition to quenching between fluorophores, individual fluorophores are also quenched by nitroxide-labeled molecules such as fatty acids. Spin labels such as nitroxides are also useful in the liquid phase assays of the invention.

In the liquid phase methods of the invention, a nucleic acid species having two labels in close proximity is contacted with a topoisomerase in the presence of a potential topoisomerase activity modulator. The first and second labels are spaced such that, upon cleavage between the two labels, the signal resulting from the labels changes. This can be easily determined empirically for any combination of label pairs, by cleaving the nucleic acids by means other than topoisomerase inhibition, using progressively longer distances between labels (i.e., by increasing the number of nucleotides between the labels), and monitoring the resulting changes in emission properties. As noted above, the literature provides $R_o$ for a large number of label pairs. Typically, the first and second labels will be between about 8 and about 40 nucleotides apart.

The liquid phase assays of the invention are performed in essentially any liquid phase containers designed for high throughput screening. Most commonly, the ligation mixture is incubated in a well on a microtiter dish (many dish formats are known, e.g., 96 well, 384 well, etc).

Compositions, Kits and Integrated Systems

The invention provides compositions, kits and integrated systems for practicing the assays described herein. For example, an assay composition having a nucleic acid topoisomerase enzyme, a tagged nucleic acid molecule comprising a tag, a topoisomerase activity modulator and a labelling moiety is provided by the present invention. Typically, in the solid phase assays, the tag binds to a tag-binding molecule fixed to a solid substrate, thereby immobilizing the tagged nucleic acid on the solid substrate. Example tags include biotin, antibodies and the like as discussed above.

Similarly, a liquid phase assay composition includes a nucleic acid topoisomerase enzyme, a nucleic acid molecule having a first label and a second label, and a topoisomerase activity modulator. As discussed in detail above, the first label is typically quenched by the second label (or the second quenched by the first) when the first and second labels are in close proximity. In the example noted above, the first label is quenched by the second label when the first label is within about 10 nm of the second label. Thus, when a topoisomerase becomes trapped in a covalent intermediate, resulting in cleavage of the nucleic acid between the two labels, the quenching is lost and an increase in signal is observed.

The invention also provides kits for practicing the methods noted above. the kits can include any of the compositions noted above, and optionally further include additional components such as instructions to practice a high-throughput method of screening for a topoisomerase inhibitor, one or more containers or compartments (e.g., to hold topoisomerase enzyme, nucleic acids, or the like), a control topoisomerase activity modulator, a robotic armature for mixing kit components or the like.

The invention also provides integrated systems for high-throughput screening of potential topoisomerase modulators for an effect on a topoisomerase. The systems typically include a robotic annature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous topoisomerase reactions.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip- compatible DOS™, OS2™ WINDOWS™, WINDOWS NT™ or WINDOWS95™ based computers), MACINTOSH™, or UNIX based (e.g., SUN™ work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

EXAMPLES

The following examples are offered to illustrate, but not to limit the present invention.

Example 1

Oligonucleotide-Based Screening Assay for Bacterial DNA Topoisomerase I

This experiment demonstrates the effectiveness of an oligonucleotide-based solid phase assay for a Type I DNA topoisomerase. The assays were performed essentially as depicted in FIG. 1, except that immune detection of the covalent topoisomerase-oligonucleotide reaction product was effected by a combination of a mouse monoclonal antibody specific for an epitope tag displayed on the DNA topoisomerase and a secondary enzyme-linked antibody directed against the mouse monoclonal antibody.

Figure 5:
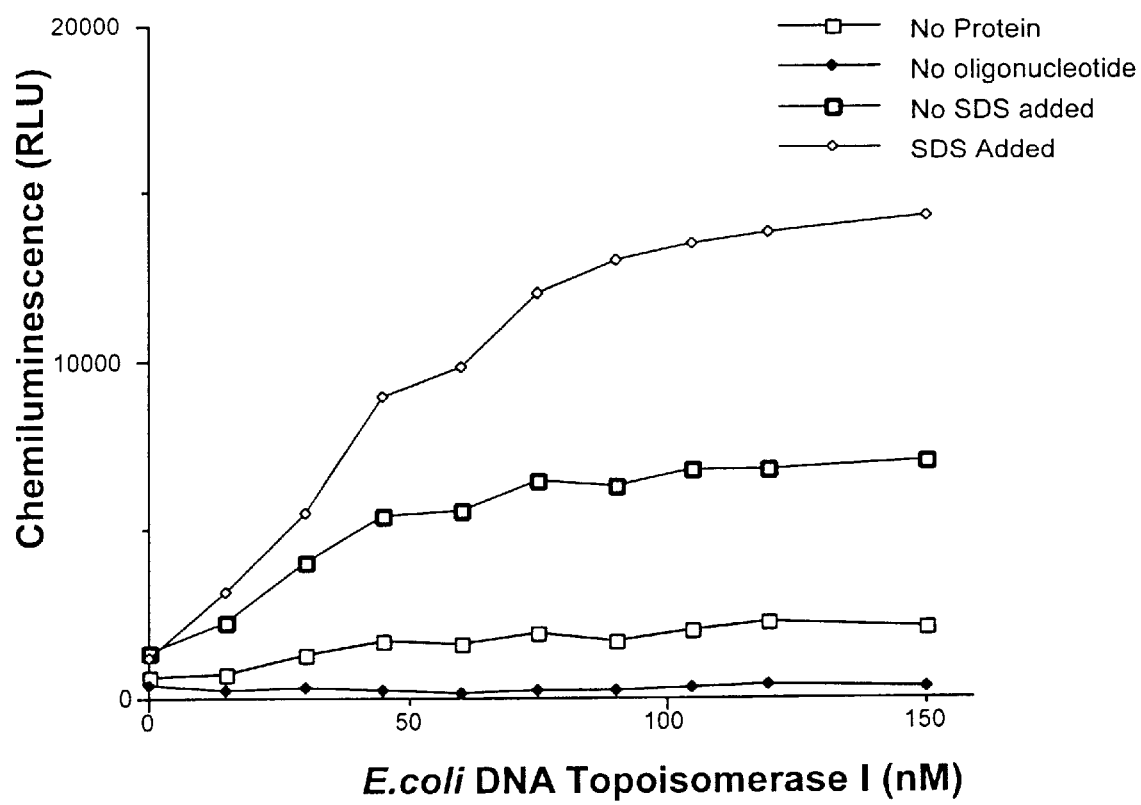
FIG. 5 provides results obtained using an oligonucleotide-based solid phase assay for E. Coli DNA topoisomerase I activity. The experiments were performed as described in Example 1 and diagrammed in FIG. 1.

| Assay conditions: | |
|---|---|
| Enzyme: | Recombinant *Escherichia coli* DNA Topoisomerase I bearing a carboxy-terminal, c-myc epitope immuno-tag (corresponding to residues 408–420 of the carboxy-terminus of the human c-myc protein). |
| Oligonucleotide substrate: | 5'-cgggatccggcgaggctggatggccttccccattatgaattcc-Biotin-3' (SEQ ID NO:1) |
| Primary antibody: | Mouse IgG$_1$-kappa antibody clone (9E10) directed against a synthetic peptide corresponding to residues 408–420 of the carboxy-terminus of the human c-myc protein (Zymed). |
| Secondary antibody: | Rabbit anti-mouse IgG antibody conjugated to horse radish peroxidase (Amersham). |
| HRP substrate: | Supersignal (Pierce). |
| Enzyme concentration: | as indicated in FIG. 5. |
| Substrate concentration: | as indicated in FIG. 5. |
| Plate: | Neutravidin coated plate (Pierce). |
| Buffer composition: | 10 mM Tris.HCl, 10 mM MgCl$_2$, 50 mM NaCl, 1 mM DTT, 0.1/μg/ml BSA (pH 7.9). |
| Other additions: | DMSO to 10% final concentration. |
| Wash Buffer: | TBS-T = Tris-buffered saline (Biorad) containing 0.05% Tween-20. |
| Readout: | luminometer; RLU = Relative Light Units. |

Methods:

Substrate oligonucleotide (30 pmol/well) was bound to the plate in TBS-T for 30 mins at 37° C. in a final volume of 100 μl, and unbound oligonucleotide removed thereafter by six sequential washings with 200 μl of TBS-T. Other components were added as indicated to give a final reaction volume of 100μl, and the reaction was then incubated for 30 mins at 37° C. One hundred μl of a 0.5% sodium dodecyl sulfate (SDS) solution was then added and the reaction incubated for 5 minutes at room temperature. The plate was then washed six times with 200 μl of a 1M NaCl solution containing 0.05% Tween 20. Two hundred μl of a 1:10,000 dilution of the primary antibody in TBS-T was added and the plate incubated at room temperature for 30 minutes, and unbound primary antibody removed thereafter by six sequential washings with 200 μl of TBS-T. Two hundred μl of a 1:10,000 dilution of the secondary antibody in TBS-T was added and the plate incubated at room temperature for 30 minutes, and unbound secondary antibody removed thereafter by six sequential washings with 200 μl of TBS-T. Detection of plate-immobilized secondary antibody was then measured by addition of 100 μl of Supersignal™ reagent and subsequent reading in a luminometer.

Results

As shown in FIG. 5, the oligonucleotide-based solid support methods of the invention provide a sensitive assay for topoisomerase I. In the example shown, the 43 base oligonucleotide utilized is a non-suicide substrate for the *E. coli* DNA topoisomerase I enzyme. However, suicide substrates for the cleavage reaction enzyme can be utilized and yield the results expected by those skilled in the art. Similarly, it will be appreciated by those skilled in the art that a compound which acts as an inhibitor of the enzyme which causes stabilization of the normal protein-DNA covalent reaction intermediate is expected to result in an increase in the intensity of the chemiluminescent signal detected.

Example 2

Oligonucleotide-Based Screening Assay for Bacterial DNA Topoisomerase IV

This experiment demonstrates the effectiveness of an oligonucleotide-based solid phase assay for a Type II DNA topoisomerase, namely *E. coli* topoisomerase IV. The assays were performed essentially as depicted in FIG. 2, except that immune detection of the covalent enzyme-oligonucleotide reaction product was effected by a combination of a mouse monoclonal antibody specific for an epitope tag displayed on the ParC subunit of DNA topoisomerase IV and a secondary enzyme-linked antibody directed against the mouse monoclonal antibody. In the example shown, the 43 bp oligonucleotide represents a suicide substrate for the DNA cleavage reaction of the *E. coli* DNA topoisomerase IV enzyme.

| Assay conditions | |
|---|---|
| Enzyme: | Recombinant *Escherichia Coli* DNA Topoisomerase IV containing a ParC subunit which bears a carboxy-terminal, c-myc epitope immuno-tag (corresponding to residues 408–420 of the carboxy-terminus of the human c-myc protein) (SEQ ID NO:1) |
| Oligonucleotide substrates: | 5'-ggaattcataatggggaaggccatccagcctcgccggatcccg-3' (SEQ ID NO:1)<br>5'-ggaattcataatggggaaggccatccagcctcgccggatcccg-3' (SEQ ID NO:2) |
| Primary antibody: | Mouse IgG$_1$-kappa antibody clone (9E10) directed against a synthetic peptide corresponding to residues 408–420 of the carboxy-terminus of the human c-myc protein (Zymed). |
| Secondary antibody: | Rabbit anti-mouse IgG antibody conjugated to horse radish peroxidase (Amersham). |
| HRP substrate: | Supersignal (Pierce). |
| Enzyme concentration: | as indicated in FIG. 5. |
| Substrate concentration: | as indicated in FIG. 5. |

| Assay conditions | |
|---|---|
| Plate: | Neutravidin coated plate (Pierce). |
| Buffer composition: | 10 mM Tris.HCl, 7 mM MgCl$_2$, 50 mM KCl, 1 mM DTT, 1 mM ATP, 1 mM spermidine (pH 7.5). |
| Other additions: | Norfloxacin (dissolved in DMSO) and added to reaction at concentrations indicated; DMSO added to 10% final concentration in all reactions. |
| Wash Buffer: | TBS-T = Tris-buffered saline (Biorad) containing 0.05% Tween-20. |
| Readout: | luminometer; RLU = Relative Light Units. |

Methods

To form the double-stranded substrate for the reaction, the two oligonucleotides were mixed in 1:2 ratio (non-biotinylated:biotinylated) in 20 mM Tris.HCl, 100 mM NaCl (pH7.5) and heated briefly to 95° C.; the mixture was then allowed to cool to room temperature over a 30–60 minute period. The annealed oligonucleotides were subsequently diluted in TBS-T and binding to the streptavidin (or neutravidin) plate effected by addition of 100 µl solution containing 10 pmol of oligonucleotides to each well and incubating for 30 mins at 37° C.; unbound oligonucleotides were removed thereafter by six sequential washings with 200 µl of TBS-T. Other components were added as indicated above to give a final reaction volume of 100 µl and the reaction was then incubated for 30 mins at 37° C. One hundred µl of a 0.5% sodium dodecyl sulfate (SDS) solution was then added and the reaction incubated for 5 minutes at room temperature. The plate was then washed six times with 200 µl of a 1 M NaCl solution containing 0.05% Tween 20. Two hundred µl of a 1:10,000 dilution of the primary antibody in TBS-T was then added and the plate incubated at room temperature for 30 minutes; unbound primary antibody was subsequently removed by six sequential washings with 200 µl of TBS-T. Two hundred µl of a 1:10,000 dilution of the secondary antibody in TBS-T was then added and the plate incubated at room temperature for 30 minutes; unbound secondary antibody similarly removed by six sequential washings with 200 µl of TBS-T. Detection of plate-immobilized secondary antibody was then measured by addition of 100 µl of Supersignal reagent and subsequent reading in a luminometer.

Results

Figure 6:
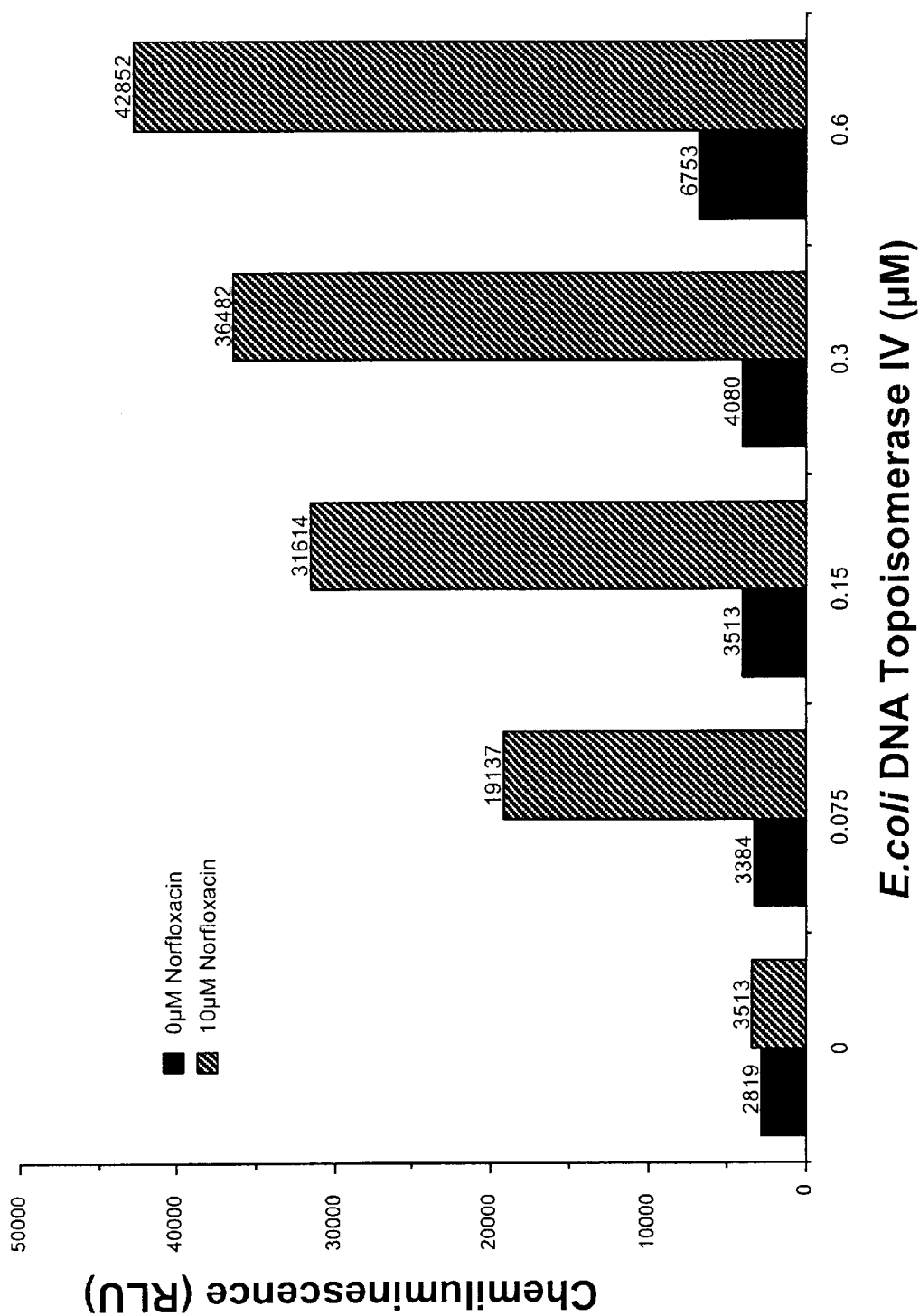
FIG. 6 shows results obtained using an oligonucleotide-based solid phase assay for E. Coli DNA topoisomerase IV activity. Experimental methods are described in Example 2 and diagrammed in FIG. 2.

The results obtained using this assay (FIG. 6) demonstrate that the oligonucleotide-based solid phase assay provides a sensitive assay for inhibition of topoisomerase IV. While the amount of signal obtained in the presence of NFX increased linearly with increasing amounts of topoisomerase, background activity in the presence of DMSO alone remained very low and was relatively independent of topoisomerase concentration.

Example 3

Plasmid-Based Screening Assay for Bacterial DNA Topoisomerase II

This experiment demonstrates the effectiveness of a plasmid-based solid phase assay for a Type II DNA topoisomerase, namely E. coli topoisomerase II. The experiments were performed essentially as depicted in FIG. 4, except that immune detection of the DNA in the final step was effected by a combination of a mouse monoclonal antibody specific for double-stranded DNA in combination with a S. aureus Protein A horse radish peroxidase (HRP) conjugate. In the example shown, the plasmid substrate used was pUC 19 (2,686 bp); numerous other plasmids up to 10,000 bp in size have been used in the assay with essentially equivalent results.

| Assay conditions | |
|---|---|
| Enzyme: | Recombinant *Escherichia coli* DNA Topoisomerase II containing a GyrA subunit which bears a carboxy-terminal, c-myc epitope immuno-tag (corresponding to residues 408–420 of the carboxy-terminus of the human c-myc protein). |
| Plasmid substrate: | pUC19. |
| Capture antibody: | A biotinylated derivative of a mouse IgG$_1$-kappa antibody clone (9E10) directed against a synthetic peptide corresponding to residues 408–420 of the carboxy-terminus of the human c-myc protein (Zymed). |
| Primary antibody: | A mouse monoclonal antibody specific for double-stranded forms of DNA (Incstar). |
| Primary antibody detection reagent: | *S. aureus* Protein A-HRP conjugate (Incstar). |
| HRP substrate: | Supersignal (Pierce). |
| Enzyme concentration: | as indicated in FIG. 5 |
| Substrate concentration: | as indicated in FIG. 5. |
| Plate: | Streptavidin coated plate (Pierce). |
| Buffer composition: | 10 mM Tris.HCl, 7 mM MgCl$_2$, 50 mM KCl, 1 mM DTT, 1 mM ATP, 1 mM spermidine (pH 7.5). |
| Other additions: | Norfloxacin or Ofloxacin (both dissolved in DMSO) and added to reaction at concentrations indicated; DMSO added to 10% final concentration in all reactions. |

| Assay conditions | |
|---|---|
| Wash Buffer: | TBS-T = Tris-buffered saline (Biorad) containing 0.05% Tween-20. |
| Readout: | luminometer; RLU = Relative Light Units. |

Methods

Reaction components were combined as indicated above and in FIG. 4 to give a final reaction volume of 100 μl, and the reaction was then incubated for one hour at 37° C. One μl of a 20% sodium dodecyl sulfate (SDS) solution was then added and the reaction incubated for five minutes at room temperature. Two hundred μl of a 1:20,000 dilution of the capture antibody in TBS-T was then added and the plate incubated at room temperature for thirty minutes. The plate was then washed three times with 200 μl of 1 M NaCl and then three times with TBS-T. Two hundred μl of a 1:500 dilution of the primary antibody in TBS-T was then added and the plate incubated at room temperature for 30 minutes, and unbound primary antibody removed thereafter by six sequential washings with 200 μl of TBS-T. Detection of plate-immobilized primary antibody was then effected by addition of the Protein A-HRP conjugate in combination with the Supersignal substrate, and chemiluminescent products detected by reading in a luminometer.

Results

Figure 7:
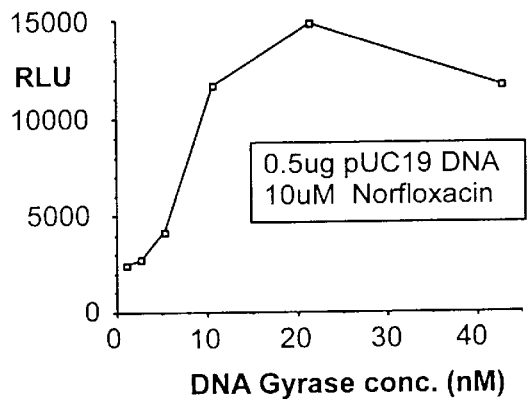
FIG. 7 shows data obtained using a plasmid-based assay for inhibition of E. Coli DNA topoisomerase II. The experiments were performed as described in Example 3 and diagrammed in FIG. 4.
Figure 7:
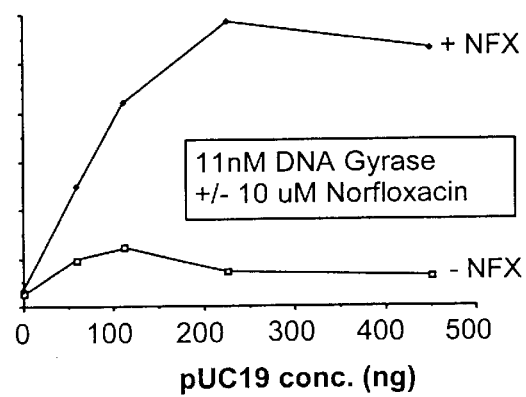
Figure 7:
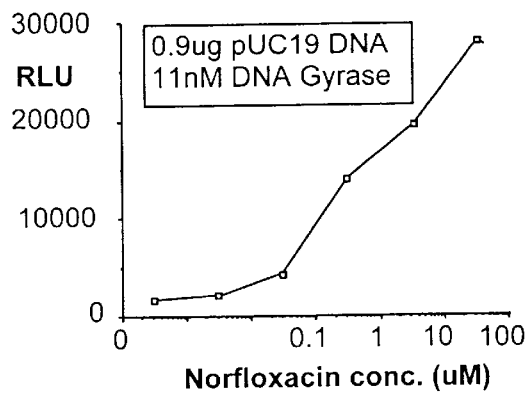
Figure 7:
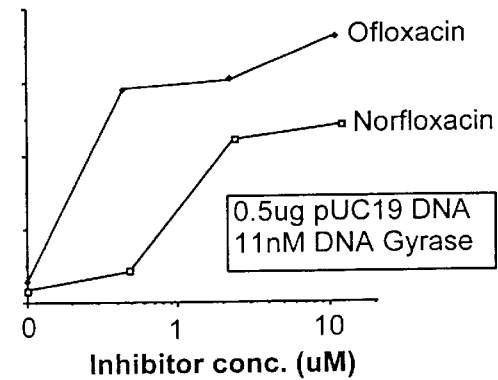

The results obtained using this assay (FIG. 7) demonstrate that the plasmid-based solid phase assay provides a sensitive assay for inhibition of topoisomerase IV. The sensitivity of the assay increases rapidly with an increase in enzyme concentration up to about 20 nM, and with an increase in template concentration up to about 200 ng, after which response levels off. The drug dose responses were relatively linear for both Ofloxacin and Norfloxacin.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of measuring the activity of a topoisomerase in the presence of a potential topoisomerase activity modulator, the method comprising:

incubating a test mixture comprising: a topoisomerase comprising an epitope, a nucleic acid, and a potential activity modulator;

adding to the test mixture a mild denaturant and an immobilization moiety which comprises a tag and a binding moiety that binds to the epitope;

binding the tag to a solid support, thereby binding the immobilization moiety to the solid support;

washing the solid support in a high salt solution to remove nucleic acid which is not bound to the immobilization moiety;

contacting the solid support-bound immobilization moiety with a labeling moiety comprising a primary label and a binding moiety that binds to the nucleic acid; and determining whether the nucleic acid is bound to the immobilization moiety by detecting the presence or absence of the labeling moiety on the solid support, thereby determining the activity of the topoisomerase in the test mixture.

2. The method of claim 1, wherein the nucleic acid is covalently closed circular plasmid DNA.

3. The method of claim 2, wherein the plasmid DNA is supercoiled.

4. The method of claim 2, wherein the plasmid DNA is relaxed.

5. The method of claim 1, wherein the nucleic acid is between about 2.5 kb and about 10 kb in length.

6. The method of claim 1, wherein the labelling moiety comprises the nucleic acid, which comprises a detectable label.

7. The method of claim 1, wherein the binding moiety is a polypeptide which binds to DNA.

8. The method of claim 7, wherein the polypeptide is an anti-DNA antibody.

9. The method of claim 1, wherein the binding moiety is a polynucleotide which hybridizes to the nucleic acid.

10. The method of claim 9, wherein the hybridization of the binding moiety to the nucleic acid forms a triplex.

11. The method of claim 1, wherein the topoisomerase is a Type I topoisomerase.

12. The method of claim 1, wherein the nucleic acid is double stranded and the topoisomerase is a Type II topoisomerase.

13. The method of claim 1, wherein incubating the test mixture comprising the potential activity modulator results in a greater amount of linkage between the tagged nucleic acid and the topoisomerase than a control mixture.

14. The method of claim 1, further comprising quantitating the amount of labeling moiety bound to the solid support.

15. The method of claim 1, wherein the test mixture comprises a plurality of topoisomerascs, each of which comprises a different epitope.

16. The method of claim 1, wherein the potential modulator is selected from the group consisting of a topoisomerase inhibitor and a topoisomerase activator.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 43 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: modified_base
       (B) LOCATION: 43
       (D) OTHER INFORMATION: /mod_base= OTHER
           /note= "N = biotinylated cytosine"

(xi) SEQUENCE DESCRIPTION: SEQ ID NO:1:

CGGGATCCGG CGAGGCTGGA TGGCCTTCCC CATTATGAAT TCN                43

(2) INFORMATION FOR SEQ ID NO:2:

(i) SEQUENCE CHARACTERISTICS:
       (A) LENGTH: 43 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

GGAATTCATA ATGGGGAAGG CCATCCAGCC TCGCCGGATC CCG                43